United States Patent
Zhang et al.

(10) Patent No.: US 12,036,077 B2
(45) Date of Patent: Jul. 16, 2024

(54) SENSOR-BASED SURGERY SET AND PROCEDURE

(71) Applicant: KARL STORZ SE & Co. KG, Tuttlingen (DE)

(72) Inventors: Yaokun Zhang, Tuttlingen (DE); Chunman Fan, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 952 days.

(21) Appl. No.: 17/065,955

(22) Filed: Oct. 8, 2020

(65) Prior Publication Data

US 2021/0113297 A1  Apr. 22, 2021

(30) Foreign Application Priority Data

Oct. 21, 2019  (DE) ..................... 10 2019 007 290.1

(51) Int. Cl.
*A61B 90/50*  (2016.01)
*A61B 17/34*  (2006.01)
(Continued)

(52) U.S. Cl.
CPC .......... *A61B 90/50* (2016.02); *A61B 17/3403* (2013.01); *A61B 34/30* (2016.02);
(Continued)

(58) Field of Classification Search
CPC ..... A61B 90/50; A61B 17/3403; A61B 34/30; A61B 90/06; A61B 2034/2048;
(Continued)

(56) References Cited

U.S. PATENT DOCUMENTS 5,697,939 A * 12/1997 Kubota .................. A61B 90/50
606/130
5,824,007 A * 10/1998 Faraz .................... F16M 11/046
600/102
(Continued)

FOREIGN PATENT DOCUMENTS

DE         19528281 A1    2/1997
DE         60313728 T2    8/2007
EP         3639782 A1     4/2020

*Primary Examiner* — Carl H Layno
*Assistant Examiner* — Manolis Pahakis
(74) *Attorney, Agent, or Firm* — Eversheds Sutherland (US) LLP

(57) ABSTRACT

The present application provides a sensor-based surgery set and a method for determining the position of a holding device for a surgical instrument. The surgery set includes at least one holding device, an initialization station, and a number of sensors. The initialization station has a number of sensor slots, wherein each sensor is assigned to one sensor slot and wherein the initialization station is coupled to a storage unit in which initialization information is assigned to each sensor slot. A number of sensor slots are arranged on the holding device, wherein each sensor slot is assigned to one sensor slot of the initialization station. In an initialization arrangement, a specific number of sensors is in engagement with the sensor slots of the initialization station and are coupled to the storage unit for initialization and data transmission. In use, however, the sensors are in engagement with the sensor slots.

10 Claims, 2 Drawing Sheets

(51) Int. Cl.
  *A61B 34/20* (2016.01)
  *A61B 34/30* (2016.01)
  *A61B 34/32* (2016.01)
  *A61B 90/00* (2016.01)

(52) U.S. Cl.
  CPC .............. *A61B 34/32* (2016.02); *A61B 90/06* (2016.02); *A61B 2034/2048* (2016.02); *A61B 2034/301* (2016.02); *A61B 2090/508* (2016.02)

(58) Field of Classification Search
  CPC ........ A61B 2034/301; A61B 2090/508; A61B 17/3421; A61B 34/20; A61B 2034/207
  See application file for complete search history.

(56) References Cited

U.S. PATENT DOCUMENTS

| | | | |
|---|---|---|---|
| 5,921,992 A * | 7/1999 | Costales | A61B 34/20 601/1 |
| 6,611,141 B1 * | 8/2003 | Schulz | A61B 34/20 324/226 |
| 7,052,455 B2 * | 5/2006 | Hale | A61B 1/0005 600/173 |
| 9,008,757 B2 * | 4/2015 | Wu | A61B 5/064 600/407 |
| 9,226,799 B2 * | 1/2016 | Lightcap | G01C 21/166 |
| 9,706,948 B2 * | 7/2017 | Bhandari | A61B 34/20 |
| 11,246,509 B2 * | 2/2022 | Bhandari | A61B 34/20 |
| 2002/0143275 A1 * | 10/2002 | Sarvazyan | A61B 5/036 600/587 |
| 2003/0109780 A1 * | 6/2003 | Coste-Maniere | G06T 7/0012 600/407 |
| 2008/0039868 A1 * | 2/2008 | Tuemmler | A61B 90/36 606/130 |
| 2011/0275957 A1 * | 11/2011 | Bhandari | A61B 5/1114 600/595 |
| 2011/0320153 A1 * | 12/2011 | Lightcap | G01C 21/166 702/94 |
| 2013/0310639 A1 * | 11/2013 | Omori | A61B 34/30 600/102 |
| 2014/0021079 A1 * | 1/2014 | Koller | A61B 50/20 206/370 |
| 2016/0220324 A1 * | 8/2016 | Tesar | A61B 90/20 |
| 2018/0199999 A1 * | 7/2018 | Syverson | A61B 17/00234 |
| 2019/0142525 A1 * | 5/2019 | Malackowski | G01S 17/86 398/115 |

* cited by examiner

SENSOR-BASED SURGERY SET AND PROCEDURE

CROSS-REFERENCE TO RELATED APPLICATIONS

This application claims the benefit of priority of German Patent Application No. DE102019007290.1 filed on Oct. 21, 2019.

TECHNICAL FIELD

The invention relates to a sensor-based surgery set and a method using the same for determining the position of a holding device for a surgical instrument during a surgical operation.

BACKGROUND OF THE INVENTION

It is known from the prior art that surgeons and entire surgical teams can be relieved during a surgical medical operation by using robot systems with which the surgical instruments used are held and controlled. However, such systems are expensive and space-consuming on the one hand, and on the other hand they create a distance between the patient and the surgeon so that the surgeon lacks the feedback on his actions as he knows it from conventional systems.

Alternatively, a surgical system can also have passive holding devices in which the surgical instruments used are only held passively, but operated manually by the surgeon, so that handling is also facilitated to a specific extent while maintaining the haptic feedback.

In order to combine the advantages of both approaches, partially automated systems must be set up. The challenge then is to couple an automatically controlled surgical instrument to the movement of a manually operated surgical instrument.

In all cases, the movement must first be precisely detected by changing the position and orientation of the holding arms and the surgical instruments, also in relation to other instruments used. The detected movement must also be interpreted correctly and, for (partial) automation, corresponding commands for controlling the robot arms that move at least one of the surgical instruments must be executed.

Calibration and registration, i.e. coupling of the movement coordinate systems of a plurality of surgical instruments, is possible by means of video sequence analysis, wherein the automatic object recognition is difficult to implement and is not reliable, especially under complex operating conditions, so that a deterministic behavior of the coupled control is not always given. An external position determination system, such as optical target tracking, can also be used. For this purpose, the instruments to be tracked must be equipped with reference bodies and no objects may block the optical detection path.

Alternatively, the detection of a position and thus indirectly the movement of surgical instruments can also be sensor-based—the sensors used must be taught-in and calibrated before use in order to generate usable measured values.

On the basis of this prior art, the object of the present invention is to provide a calibratable surgery set that allows the position and orientation of a holding device for a surgical instrument to be reliably detected. This object is achieved by a sensor-based surgery set with the features in accordance with claim 1.

The further object of reliably and reproducibly determining the position of a holding device for a surgical instrument during a surgical operation is achieved by the method using the surgery set with the features of independent claim 9.

Preferred embodiments of the surgery set and the method are set out in the dependent claims.

SUMMARY OF THE INVENTION

In a first embodiment of a sensor-based surgery set according to the invention, this comprises at least one holding device for a surgical instrument, an initialization station, and a plurality of sensors. The initialization station has a corresponding number, in other words, "a plurality," of sensor slots (hereinafter also referred to as initialization slots) with which the sensors can be brought into engagement, wherein exactly one initialization slot is clearly assigned to each sensor. The initialization station is also coupled to a storage unit in which initialization information is assigned to each initialization slot. The initialization station can have the storage unit directly, with the storage unit also being part of a distributed storage system. Alternatively, the storage unit can be present externally in a central data storage. A plurality of sensor slots are arranged on the holding device (hereinafter also referred to as holding slots) with which the sensors can be brought into engagement, wherein exactly one sensor slot of the initialization station is clearly assigned to each sensor slot of the holding device. In this case, in an initialization arrangement of the surgery set, a specific number of sensors is in engagement with the sensor slots of the initialization station and is coupled to the storage unit for initialization and data transmission. In a usage arrangement of the surgery set, the sensors intended for use are in engagement with the sensor slots of the holding device.

The surgical instrument is an instrument with which an action, e.g., manipulation, analysis, or imaging, can be performed during a surgical operation such as a laparoscopic operation. In the present case, "surgical" can also be understood as "microsurgical" throughout the text. In particular, it can also be a microsurgical instrument for carrying out a microsurgical operation. The surgical instrument can also comprise a trocar, via which access to the treatment location located in the patient's body is provided.

A "passive" holding device is understood in this case to mean a holding device for a surgical instrument, it also being possible for the holding device to be held indirectly via a trocar, via which the instrument can be actuated. The surgical instrument is operated manually, i.e., the holding device, in contrast to an "active" holding device, has no components for the automated or remote-controlled actuation of the instrument. Instruments controllable by active holding devices are also referred to herein as "automatically controlled" instruments, in contrast to "manually controlled" instruments. The positioning and actuation of the holding device, on the other hand, can be motorized and also automated in both cases.

The assignment of initialization slots to holding slots or of sensors to the respective sensor slots is initially given by naming and linking with corresponding initialization information. This "initialization information" includes all information or data that are required to teach-in the sensors, including properties inherent to the sensor, the alignment of the initialization slot as a reference (defined as the zero position in three-dimensional space), and the assignment to the holding slot. Copies of this initialization information can be stored locally or centrally both in the respective sensor and in the storage unit. Depending on its intended use, a sensor can be arranged on the holding device of the surgical instrument at a predetermined initialization slot. It is crucial that the sensor, the initialization information of which is detected or transmitted and stored, is brought into engagement with the associated holding slot in the usage arrangement, so that when there is movement, i.e., changes in position, the appropriate initialization information is used as a reference. By referring to the zero position specified by the initialization slot, the position of each individual sensor can be calculated at any time from the data collected by the sensors. Since the assigned holding slot on the surgical instrument or the holding device is clearly determined and known, the position, i.e., the orientation of the instrument three-dimensional space, can be derived and tracked.

The calculation as well as the storage of the reference position and further initialization information can take place in a data processing unit in a central control system, with which control commands can also be derived, sent, and executed.

The surgery set according to the invention can be brought into the initialization arrangement in order to initialize the sensors, i.e., to record calibration and initialization information and/or to pick up data from the sensor and store them as initialization information in the storage unit of the initialization station. A "specific number" is predetermined by the user and depends on how many surgical instruments are to be tracked and how many sensors per instrument are to be attached to the respective holding devices. It can correspond at most to the number of initialization slots.

The set can include more sensors than are necessary for a specific surgical operation; these can, for example, be placed in the initialization station and remain there, while only the sensors intended for use are attached to the holding slots.

Advantageously, the sensor-based surgery set creates a possibility to reliably determine the position of a holding device for a surgical instrument with little effort and thus indirectly also the position of a surgical instrument guided therein and its current position by means of sensor units because optical units that are susceptible to failure can be dispensed with. Due to the common initialization of the sensors before they are used and the unambiguous assignment of initialization information to predetermined holding slots, any change in position detected by the sensors relative to the initialization can be measured and correctly interpreted in current position or orientation information of the holding device or the surgical instrument.

Time-consuming teach-in of the sensors, which requires trained personnel, is therefore also not necessary. Placing the sensors in the initialization station for initialization and then placing them in the holding slots is a procedure that rarely leads to errors.

Furthermore, the position and orientation information determined in this way can also be used for the determination of the relative alignment of a plurality of surgical instruments with one another. The surgery set can comprise a plurality of holding devices, with the position being determined via the initialized sensors for both active and passive holding devices or instruments held therein or only for instruments held passively. In the case of automatically controlled surgical instruments, the position of the holding device and the instrument is substantially determined by the control commands, but in order to check whether these have been correctly implemented and to correct any deviations, it is also necessary to determine the position and orientation using sensors.

A further embodiment of the surgery set according to the invention provides that the sensor slots of the initialization station are aligned in a common, matching reference direction. Regardless of how the initialization station itself is arranged, if the sensors are placed in the initialization slots in the initialization arrangement of the surgery set, they are also aligned in this common reference direction (zero position in three-dimensional space) which is stored for the entire following operation. As a result, the alignment of the sensors in the usage arrangement can be determined via the measured value detected by the sensors with respect to this common reference direction. Since the reference direction coincides, the computational effort is significantly reduced in order to determine the position of the sensors and thus the holding device. The transmission of the data as input into a further coordinate system in order to control a further, automatically controlled surgical instrument can also be carried out more easily, or associated control signals can be derived more easily.

In a further embodiment, the surgery set further comprises at least one surgical instrument, which is received in the usage arrangement in the holding device. In this way, the sensors can also be used to determine the orientation and position of the surgical instrument, in addition to determining the position of the holding device. In particular, sensors that are attached to the holding device can interact with the surgical instrument and thereby even acquire information about the surgical instrument which is not directly linked to the position of the holding device, for example a displacement of the surgical instrument relative to the holding device.

According to another embodiment, the surgery set comprises at least two holding devices and two surgical instruments. Of these, a first holding device is a passive holding device and a first surgical instrument is a manually controlled surgical instrument which is received in the usage arrangement in the passive holding device. A second holding device is an active holding device and a second surgical instrument is an automatically controlled surgical instrument which is received in the usage arrangement in the active holding device. The active holding device can, for example, be a robot arm of a surgical robot known from the prior art.

The sensor data, in particular the passive holding device, can thus be used as input for the control of the automatically controlled surgical instrument, because the coupling of each movement coordinate system of the instruments advantageously takes place via a "registration," i.e., already when the sensors are initialized with the transmission of the initialization information. The coordinates, which are described via the position and orientation of the manually controlled surgical instrument, can thus be easily interpreted with respect to the coordinate system of the automatically controlled surgical instrument. Consequently, the position of the passively held, manually controlled surgical instrument(s) can be correctly interpreted relative to one another and relative to the orientation of the automatically controlled instrument. In a particularly preferred embodiment of the set, the automatically controlled instrument is an endoscope. The surgeon then focuses on relevant body regions by moving the other surgical instruments, and the visual representation is coupled to this without manual intervention.

In a further embodiment, the at least one holding device of the surgery set is a passive holding device which has a fastening device with a coupling portion, wherein a trocar that holds or guides the surgical instrument during a surgical operation can be fastened via a trocar holder to a connecting device and can be fastened to the fastening device via said connecting device. A pivoting mechanism which is connected to the coupling portion via a rotary joint located in the coupling portion so as to be rotatable about a horizontal axis of the coupling portion forms the connecting device. The pivoting mechanism has two L-shaped branches arranged parallel to one another, each of which has a short leg which is connected to a long leg via a pivot joint. On the coupling portion side, the ends of the short legs of each branch lying next to one another are connected to an elongated holding portion of the fastening device via a terminal pivot joint. The short leg of the first branch is longer than the short leg of the second branch, is arranged at a distal end of the elongated holding portion, and is connected to the long leg of the second branch via a rotary shaft. The trocar holder is pivotably attached to a distal end of the pivoting mechanism and has a gripping device which can be brought into engagement with the trocar and which has an instrument brake for the operative coupling with the surgical instrument. A tilting brake is arranged at a proximal end of the coupling portion and is operatively connected to the rotary joint located in the coupling portion. A pivoting brake is also arranged on the coupling portion and is operatively connected to at least one of the terminal pivot joints of the pivoting mechanism. In the usage arrangement, the trocar is engaged with the gripping device and the surgical instrument is received in the trocar.

The terms "proximal" and "distal" are to be understood in relation to the user, e.g. a surgeon, i.e., "distal" is further away from the user in normal use, whereas "proximal" is closer to the user. This passive holding device provides a stationary rotary point for the trocar and thus for the surgical instrument, which can be placed directly in the surgical point of entry in a patient. The sensors or the part of the sensors can be arranged on the joints of the holding device in the application arrangement of the surgery set, which are provided for determining the position of the passive holding device, and thus also serve to determine the orientation and position of the surgical instrument held in this holding device.

The content of patent application DE 10 2019 128 277.2 is incorporated in the present application in its entirety by reference.

According to a further embodiment, the sensor slots of the holding device for the surgical instrument are adapters for the sensors. The holding slots can be adapted via the adapter, which can preferably be arranged interchangeably on the holding device of the surgical instrument, so that the unambiguous assignment is given and can nevertheless be designed in a variable manner. It is also possible via the adapter to clearly predetermine the alignment of the holding slots, which can be integrated into the initialization information of the sensor attached in the usage arrangement. The alignment relative to the initialization alignment is then already known for a starting position of the holding device, and thus also of the surgical instrument when it is brought into the holding device for the usage arrangement. Furthermore, the adapter or the holding slots and the initialization slots can be coordinated with one another in such a way that, for example, depending on the shape, only the respectively assigned sensors can be arranged at these points, thereby avoiding errors in attachment.

In yet another embodiment, the sensors are inertial sensors, in particular position, acceleration, or rotation rate sensors, or inertial measuring units. In this case, sensors can be understood to be both individual sensors and sensor bundles already combined to form a measuring unit, which are consequently calibrated jointly to a reference alignment in the initialization station. An at least six-axis sensor, which comprises a three-axis gyrometer and a three-axis acceleration sensor, is preferably used, the measurement data of which are combined in order to calculate the current position/orientation. In addition, a three-axis magnetometer can be provided as part of the sensor, which increases the accuracy of the values determined.

According to yet another embodiment, the initialization station is a sterilizable initialization container. Thus, in addition to the actual initialization of the sensors in the initialization arrangement, sterilization, which is necessary for hygienic treatments, can take place immediately. Containers for reprocessing, i.e., preparation and sterilization, are known for surgical, for example laparoscopic, instruments, with corresponding spaces being available for the instruments. The initialization container of the invention has a similar structure and provides the slots for the sensors. The initialization container can thus also be used to store the sensors between surgical operations and the sensors do not have to be subjected to further treatments before and/or after initialization.

The sensors themselves can be produced for single use and can be sterilized by known methods, for example ethylene oxide sterilization (EO) or radiation sterilization with beta or gamma radiation. Alternatively, sensors designed for multiple use can be used which, after being used in the usage arrangement of the surgery set, are subjected to reprocessing without being damaged in the process. For this purpose, the sensors can be protected in a sealed housing.

According to one embodiment of the method according to the invention for determining the position of the at least one holding device for the surgical instrument during a surgical operation, this is carried out using the sensor-based surgery set. It comprises the following steps:

arranging the sensors in the slots of the initialization station, activating the sensors, initializing the sensors by transferring initialization information between the storage unit and the sensors, detaching the sensors from the slots of the initialization station and arranging the sensors in the slots of the holding device for the surgical instrument, operating the at least one holding device, thereby comparing the current position of the sensors with the initialization information, thereby determining the current position of the holding device.

By determining the position of the holding device, i.e., the position in space and the orientation, it can be checked whether the control for positioning has taken place as intended. Furthermore, the position, including the orientation, location, and alignment of the surgical instrument when it is actuated in the holding device, can also be calculated from this. If the surgical instrument is fastened to the holding device via a trocar, the position of the trocar and, from this, the position of the surgical instrument can first be determined. Sensors can also be arranged on the holding device in such a way that a change in the position of the surgical instrument relative to the holding device can be detected. Such changes are included in the sensor-detected position of the holding device.

No special qualifications of the personnel in sensor reprocessing are required to carry out the method. In the simplest case, activating the sensors takes place in preparation for use, in particular in preparation for a surgical operation, simply by starting the power supply to the sensors. The transmission of initialization information can be done in both directions, i.e., information about the sensor can be determined or read out and stored in the storage unit and/or information can be transferred to the sensor. "Operating" the holding device includes in particular the positioning or repositioning, and thereby changing the current position of the holding device that is to be digitally detected. The position of the sensors includes the measured values detected by the sensors, which are used to determine the position. The position of the holding device determined in this way can be used for various purposes, e.g., for data processing, visualization of the position, as input for a coupled instrument control or storage for subsequent or simultaneous analysis of the entire movement sequence.

The sensors can be put back into the initialization station immediately after the surgical operation, so that it is also used for storage, or can be put back only immediately before the next use. After the arrangement in the initialization station, a sterilization step can be carried out.

Another embodiment of the method comprises the steps
when initializing the sensors, calibrating the sensors to a common reference position and
when comparing the current position of the sensors with the initialization information, comparing the current position of the sensors with the common reference position. This considerably reduces the computational effort; the prerequisite is the common reference position of the sensors, which can be determined via slots of the initialization station aligned in a common reference direction.

Another embodiment of the method is carried out with a surgery set according to the invention which has at least one passive holding device and a manually controlled surgical instrument as well as an active holding device and an automatically controlled surgical instrument, wherein the manually controlled surgical instrument is received in the passive holding device and the automatically controlled surgical instrument is received in the active holding device in the usage arrangement. The method is used to determine at least the position of the passive holding device and also the position of the manually controlled surgical instrument. The following steps are carried out when operating the passive holding device:

optional actuating of the manually controlled surgical instrument and thereby
calculating the position of the passive holding device and/or the position of the manually controlled surgical instrument relative to the position of the active holding device and/or the position of the automatically controlled surgical instrument,
deriving control signals therefrom in order to control the automatically controlled surgical instrument depending on the position of the passive holding device and/or the position of the manually controlled surgical instrument,
using the active holding device to control the automatically controlled surgical instrument with the derived control signals.

This embodiment of the method takes advantage of the fact that the position of the surgical instruments in relation to one another is easy to determine since the sensors were calibrated together in the initialization station. The calculatory effort for deriving the control signals is lower and the susceptibility to errors is reduced. The automatically controlled instrument, preferably an endoscope, does not have to be positioned by the surgeon or other personnel who have to be instructed accordingly and nevertheless focuses on the relevant region. For the surgeon, work is made easier in a conventional operating environment.

Further embodiments as well as some of the advantages associated with these and further embodiments will be made clearer and better understood from the following detailed description with reference to the accompanying drawings. Objects or parts thereof that are substantially the same or similar can be provided with the same reference signs. The drawings are only a schematic representation of an embodiment of the invention.

DETAILED DESCRIPTION

The invention relates to a sensor-based surgery set 1 that is used in a method for determining the position of at least one holding device 8, 80 for a surgical instrument 2, 20 during a surgical operation.

Figure 1:
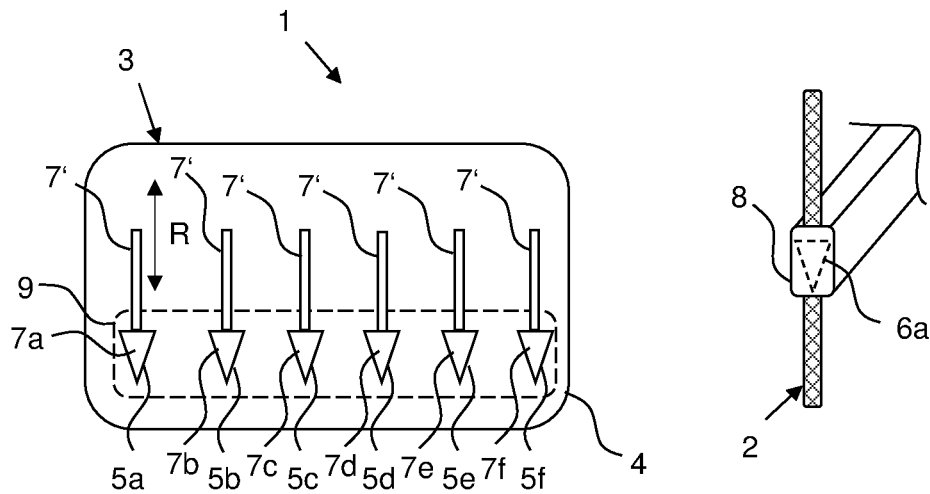
FIG. 1 is a view of the surgery set in the initialization arrangement.

FIGS. 1 and 2 show an exemplary surgery set 1 that has an initialization station 3, a passive holding device 8, and six sensors 7a, 7b, 7c, 7d, 7e, 7f, which for better differentiation from the sensor slots 5a, 5b, 5c, 5d, 5e, 5f and 6a are shown with power lines 7'; the energy supply of the sensors 7a, 7b, 7c, 7d, 7e, 7f can also take place in other ways. A section of a passive holding device 8 and a surgical instrument 2 is also shown only symbolically, the surgical instrument 2 being arranged in the holding device 8. For the initialization arrangement, however, it is not customary for a surgical instrument 2 to be held in the holding device 8; this representation serves to visualize the free holding slots 6a on the holding device 8.

An example of a passive holding device is described in DE 10 2019 128 277.2, to which reference is made in full.

The surgical instrument 2 can already be provided as part of the set 1. Basically, however, any surgical instruments, provided they can be held and operated in the respective holding device, are suitable for use with the set 1 and can therefore be selected later.

In the initialization station 3, six slots 5a, 5b, 5c, 5d, 5e, 5f are provided, which are brought into engagement with the six sensors 7a, 7b, 7c, 7d, 7e, 7f in the initialization arrangement. The initialization station 3 also has a storage unit 9 (dashed), which can be operatively coupled to a comprehensive data processing unit (not shown) or also be part of such. As an alternative to the embodiment shown, the storage unit 9 can also be present outside the initialization station 3 as part of a central data storage and is coupled to the initialization station 3 for data transmission.

In the initialization arrangement, the sensors 7a, 7b, 7c, 7d, 7e, 7f are in communication with the storage unit 9 after the initialization station 3 and/or the sensors 7a, 7b, 7c, 7d, 7e, 7f have been activated. They then transmit the initialization information alternately or in one direction, which is individually assigned to the respective sensor 7a, 7b, 7c, 7d, 7e, 7f and the respectively assigned initialization slot 5a, 5b, 5c, 5d, 5e, 5f. The holding slots—only one holding slot 6a assigned to the initialization slot 5a is shown here—are provided on joints, arms, or other locations of the holding device 8, or can be formed by adapters which are detachably connected to the holding device. Further holding slots cannot be seen but they can be present in a region of the holding device 8 (not shown) or be provided on other holding devices that are used in other uses of the set 1, such as other types of surgical operations. The initialization slots 5a, 5b, 5c, 5d, 5e, 5f are assigned to specific holding slots 6a, 6d (FIG. 3), i.e., the initialization slot 5a is assigned to the holding slot 6a, the initialization slot 5d is assigned to the holding slot 6d, etc. The adapters that form the holding slots 6a, 6d are unoccupied in the initialization arrangement (unoccupied slots 5a, 5b, 5c, 5d, 5e, 5f and 6a are each shown in dashed lines).

After the initialization has taken place, the set 1 is transferred to the usage arrangement (FIG. 2a) by removing the sensors 7a, 7b, 7c, 7d, 7e, 7f from the slots 5a, 5b, 5c, 5d, 5e, 5f of the initialization station 3 and arranging them at the associated slots 6a of the holding device 8. Only one sensor 7a is shown in the slot 6a of the holding device, which has previously been initialized according to the slot 5a of the initialization station 3. The further sensors 7b, 7c, 7d, 7e, 7f can be in engagement with other slots of the holding device 8, not shown in this view of the holding device 8. However, not all sensors 7a, 7b, 7c, 7d, 7e, 7f of the set 1, regardless of whether they have been initialized or not, are attached to the holding device 8 in the usage arrangement, so they can remain (temporarily) unused.

Figure 2A:
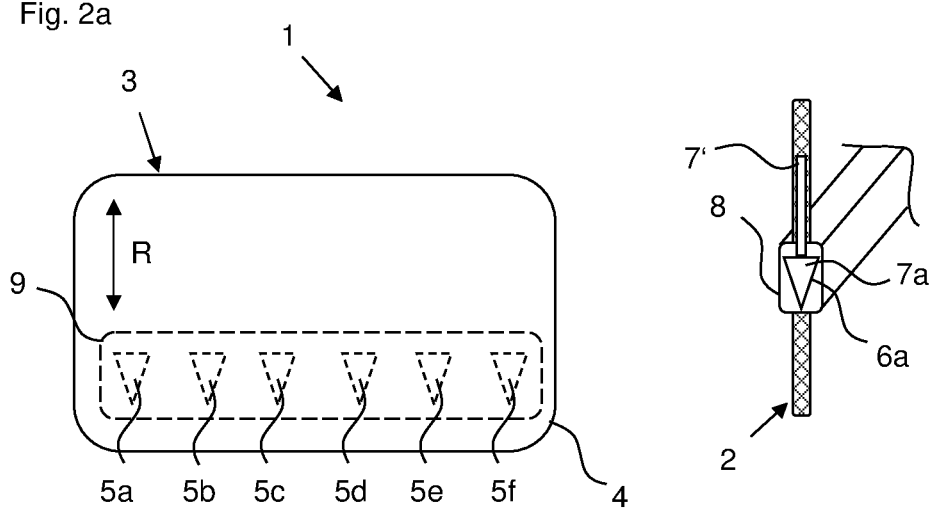
FIG. 2 is a view of the surgery set in the usage arrangement, with a holding device a) in the starting position and b) in a changed position.
Figure 2B:
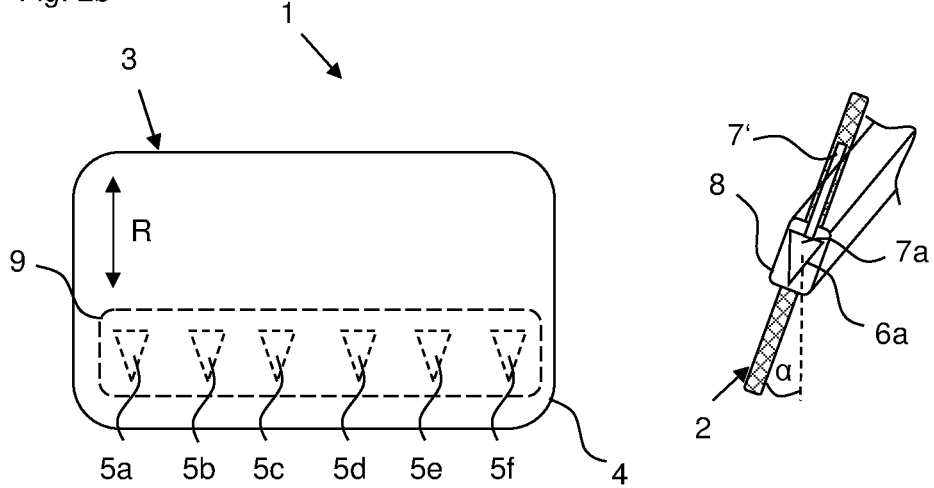

In the comparison of FIG. 2a to FIG. 2b, a change in position of the holding device 8 is shown; in the example, a change by the angle of change of position α, which is triggered when the holding device 8 is operated and which is usually transferred to the surgical instrument 2 that is held, is shown. Each such change in position is detected as a relative change in position with respect to the starting position by sensor 7a (for example, the position in FIG. 2a can be defined as the starting position). This already valuable information about the positioning of the holding device 8 can also be used to calculate the position of the surgical instrument 2.

In the embodiment shown, all initialization slots 5a, 5b, 5c, 5d, 5e, 5f are aligned along a common, matching reference direction R, i.e., a common "zero point" for all sensors 7a, 7b, 7c, 7d, 7e, 7f is set as a common starting position, so that this parameter dimension is predetermined by the initialization arrangement and can be used as a relative point for determining the position for all sensors 7a, 7b, 7c, 7d, 7e, 7f.

The initialization station 3 is enclosed in a housing 4 so that a sterilization of the interior of the housing and the sensors 7a, 7b, 7c, 7d, 7e, 7f placed therein can also take place within the initialization station 3. The housing 4 also protects the sensors 7a, 7b, 7c, 7d, 7e, 7f from external influences and can generally be stored in the initialization station 3 when not in use, regardless of the initialization.

The number of slots 5a, 5b, 5c, 5d, 5e, 5f in the initialization station 3 can also be varied, as can the number of sensors 7a, 7b, 7c, 7d, 7e, 7f, wherein it is useful, but not absolutely necessary, that the number of slots 5a, 5b, 5c, 5d, 5e, 5f of the initialization station 3 corresponds to the number of sensors 7a, 7b, 7c, 7d, 7e, 7f. The number of holding devices 8 and the holding slots 6a, 6d arranged there are also variable and also depend on whether the sensors 7a, 7b, 7c, 7d, 7e, 7f already form an integrated measuring unit, which can detect a plurality of physical variables in combination, or whether individual sensors are used, of which a larger number in the usage arrangement of the surgery set 1 are in engagement with the slots 6a, 6d of the holding device 8.

Figure 3:
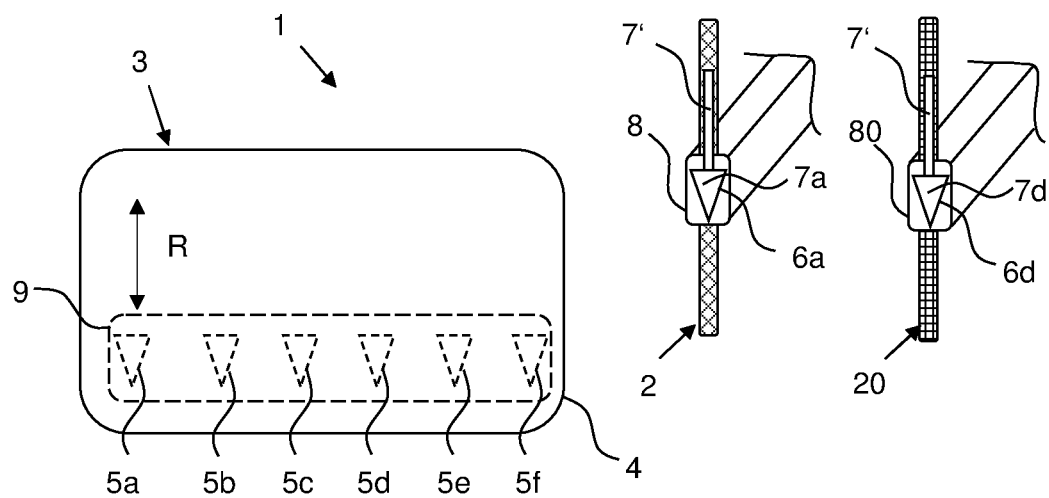
FIG. 3 is a view of a further embodiment of the surgery set in usage arrangement.

FIG. 3 shows an embodiment of the surgery set 1 in a usage arrangement by way of example which, in addition to the initialization station 3 having the initialization slots 5a, 5b, 5c, 5d, 5e, 5f, includes two holding devices 8, 80, wherein a passive holding device 8 holds a manually controlled surgical instrument 2 and an active holding device 80 holds an automatically controlled surgical instrument 20. The sensor 7a is attached to the holding slot 6a of the passive holding device 8, which is provided by an adapter, and is thus initialized according to the initialization slot 5a. The sensor 7d is attached to the holding slot 6d, likewise an adapter, of the active holding device 80; i.e., was previously initialized according to the initialization slot 5d. Now, it is not only possible to detect the change in position of a holding device 8, 80 for itself, but also their relative orientation to one another, which makes it easier to implement different modes for controlling, in particular, the automatically controlled instrument 20. In other words, control commands for the active holding device 80 or the instrument 20 held therein can be derived from the detected change in position of the passive holding device 8 in order to couple the movement of the two instruments 2, 20 to one another. An application example for this is an automatically controlled endoscope that follows the orientation specified by the surgeon on a manually controlled instrument and thus supports a manually performed surgical operation.

An even larger number, for example three, four, or five holding devices, can easily be equipped with sensors that can be arranged and initialized in the initialization station. It is not excluded to use holding devices without holding slots or adapters in addition to the holding devices equipped with sensors as part of the set.

LIST OF REFERENCE SIGNS

1 Surgery set
2 Manually controlled surgical instrument
3 Initialization station
4 Housing
5a, 5b, 5c, 5d, 5e, 5f Initialization slot
6a, 6d Holding slot
7a, 7b, 7c, 7d, 7e, 7f Sensor
7' Power line sensor
8 Passive holding device
9 Storage unit
20 Automatically controlled surgical instrument
80 Active holding device
R Reference direction
α Angle of change of position It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

We claim:

1. Sensor-based surgery set comprising: at least one holding device for a surgical instrument, an initialization station, and a plurality of sensors, wherein
the initialization station has a plurality of sensor slots with which the sensors can be brought into plug engagement, wherein each sensor is explicitly assigned to exactly one sensor slot and wherein the initialization station is coupled to a storage unit in which initialization information is assigned to each sensor slot, and wherein a plurality of sensor slots is arranged on the holding device, with which the sensors can be brought into plug engagement, wherein each sensor slot of the holding device is explicitly assigned to exactly one sensor slot of the initialization station, wherein in an initialization arrangement of the surgery set, a specific number of sensors is in plug engagement with the sensor slots of the initialization station and is coupled to the storage unit for initialization and data transmission, wherein in a usage arrangement of the surgery set, the sensors determined for use are plug engaged with the sensor slots of the holding device, and wherein the sensors are inertial sensors or inertial measuring units.

2. Surgery set according to claim 1, characterized in that the sensor slots of the initialization station are aligned in a common, matching reference direction.

3. Surgery set according to claim 1, characterized in that the set further comprises at least one surgical instrument, which is received in the usage arrangement in the holding device.

4. Surgery set according to claim 3, characterized in that at least two holding devices and two surgical instruments are present, wherein a first holding device is a passive holding device and a first surgical instrument is a manually controlled surgical instrument which is received in the usage arrangement in the passive holding device, and a second holding device is an active holding device and a second surgical instrument is an automatically controlled surgical instrument which is received in the usage arrangement in the active holding device.

5. Surgery set according to claim 1, characterized in that the at least one holding device is a passive holding device which has a fastening device with a coupling portion, wherein a trocar that holds or guides the surgical instrument during a surgical operation can be fastened via a trocar holder to a connecting device and can be fastened to the fastening device via said connecting device, wherein a pivoting mechanism is connected to the coupling portion via a rotary joint located in the coupling portion so as to be rotatable about a horizontal axis of the coupling portion and forms the connecting device, wherein the pivoting mechanism has two L-shaped branches arranged parallel to one another, each of which has one short leg which is connected to a long leg via a pivot joint, wherein, on the coupling portion side, the ends of the short legs of each branch lying next to one another are connected to an elongated holding portion of the fastening device via a terminal pivot joint, and wherein the short leg of the first branch is longer than the short leg of the second branch, is arranged at a distal end of the elongated holding portion, and is connected to the long leg of the second branch via a rotary shaft, and wherein the trocar holder, which has a gripping device which can be brought into engagement with the trocar, and which has an instrument brake for the operative coupling with the surgical instrument, is pivotably attached to a distal end of the pivoting mechanism, and wherein a tilting brake is arranged at a proximal end of the coupling portion and is operatively connected to the rotary joint located in the coupling portion, and a pivoting brake is arranged on the coupling portion, which is operatively connected to at least one of the terminal pivot joints of the pivoting mechanism.

6. Surgery set according to claim 1, characterized in that the sensor slots of the holding device are adapters for the sensors.

7. Surgery set according to claim 1, characterized in that the initialization station is a sterilizable initialization container.

8. Method for determining the position of a holding device for a surgical instrument during a surgical operation using a surgery set according to claim 1, comprising the steps of arranging the sensors in the slots of the initialization station, activating the sensors, initializing the sensors by transferring initialization information between the storage unit and the sensors, detaching the sensors from the slots of the initialization station and arranging the sensors in the slots of the holding device for the surgical instrument, operating the at least one holding device, thereby comparing the current position of the sensors with the initialization information, thereby determining the current position of the holding device.

9. Method according to claim 8, comprising the steps of when initializing the sensors, calibrating the sensors to a common reference position and when comparing the current position of the sensors with the initialization information, comparing the current position of the sensors with the common reference location.

10. Method according to claim 8, wherein the surgery set has at least one passive holding device and a manually controlled surgical instrument as well as an active holding device and an automatically controlled surgical instrument, wherein the manually controlled surgical instrument is received in the passive holding device and the automatically controlled surgical instrument is received in the active holding device in the usage arrangement, comprising the steps of when operating the passive holding device, optionally operating the manually controlled surgical instrument and thereby calculating the position of the passive holding device and/or the position of the manually controlled surgical instrument relative to the position of the active holding device and/or the position of the automatically controlled surgical instrument, deriving control signals therefrom in order to control the automatically controlled surgical instrument depending on the position of the passive holding device and/or the position of the manually controlled surgical instrument, using the active holding device to control the automatically controlled surgical instrument with the derived control signals.

\* \* \* \* \*